US00RE42090E

(19) United States
(12) Reissued Patent
Bruner et al.

(10) Patent Number: US RE42,090 E
(45) Date of Reissued Patent: Feb. 1, 2011

(54) METHOD OF SORTING WASTE PAPER

(75) Inventors: Russell S. Bruner, Franklin, TN (US); David R. Morgan, Hardin, KY (US); Garry R. Kenny, Nashville, TN (US); Paul G. Gaddis, Seattle, WA (US); David Lee, Tacoma, WA (US); James M. Roggow, Puyallup, WA (US)

(73) Assignee: MSS, Inc., Nashville, TN (US)

(21) Appl. No.: 11/139,005

(22) Filed: May 26, 2005

Related U.S. Patent Documents

Reissue of:
(64) Patent No.: 6,570,653
Issued: May 27, 2003
Appl. No.: 10/004,690
Filed: Dec. 4, 2001

U.S. Applications:

(63) Continuation of application No. 09/301,715, filed on Apr. 29, 1999, now Pat. No. 6,369,882.

(51) Int. Cl.
*G01N 21/64* (2006.01)

(52) U.S. Cl. ..... 356/417; 356/317; 250/459.1; 250/461.1; 209/577

(58) Field of Classification Search ..... 356/317, 356/417; 250/458.1, 459.1, 461.1, 461.2; 209/577
See application file for complete search history.

(56) References Cited

U.S. PATENT DOCUMENTS 1,035,345 A 8/1912 Heess (Continued)

FOREIGN PATENT DOCUMENTS

CA 2109021 4/1994

(Continued)

OTHER PUBLICATIONS

Exhibit A: U.S. Appl. No. 09/516,257, filed Feb. 29, 2000 (now U.S. Patent No. 7,019,822) and its file history.

(Continued)

*Primary Examiner*—F. L Evans
(74) *Attorney, Agent, or Firm*—Waddey & Patterson, P.C.; Lucian Wayne Beavers

(57) ABSTRACT

[Apparatus and methods are provided for sensing the presence of bright white paper on a conveyor of a paper sorting system. The conveyor is constantly illuminated with ultraviolet light. When bright white paper is present in the inspection zone of the conveyor, it will re-radiate fluorescent light energy as a result of the ultraviolet light. Periodically, the inspection zone of the conveyor is illuminated with a second light source in the visible light spectrum. Light is collected from the inspection zone of the conveyor, including reflected light from the secondary source and including emitted fluorescent light energy as a result of the ultraviolet light falling on bright white paper. Periodically a microprocessor associated with the sensor senses reflected light from the second source to determine whether any object if present on the conveyor. The microprocessor then senses the level of fluorescent light energy being emitted from any object on the conveyor. The system determines first whether any object is present on the conveyor, as a result of the reflected secondary light, and then determines whether that object is bright white paper depending upon the measured level of emitted fluorescent light energy. Based upon these determinations, the stream of waste paper on the conveyor can be sorted into two fractions, one of which is the bright white paper.] *A method of sorting waste paper includes spreading waste paper out into a layer that is substantially one unit thick; detecting the presence or absence of a predetermined optical characteristic as the layer of paper is passed by a sensor; and controlling one or more actuators that direct a sheet of paper based on the presence or absence of the predetermined optical characteristic.*

30 Claims, 8 Drawing Sheets

U.S. PATENT DOCUMENTS

| | | | | | |
|---|---|---|---|---|---|
| 1,547,743 | A | | 7/1925 | Fowler | |
| 1,847,263 | A | | 3/1932 | Sandberg | |
| 1,847,265 | A | | 3/1932 | Sandberg | |
| 2,897,952 | A | | 8/1959 | Buccicone | |
| 3,101,832 | A | | 8/1963 | Wyle et al. | |
| 3,185,286 | A | | 5/1965 | Koplin | |
| 3,198,352 | A | | 8/1965 | Puechberty | |
| 3,227,263 | A | | 1/1966 | Kastenbein | |
| 3,352,404 | A | | 11/1967 | Settembrini | |
| 3,471,013 | A | | 10/1969 | Haver | |
| 3,606,645 | A | | 9/1971 | Hardy | |
| 3,650,369 | A | | 3/1972 | Vergobbi | |
| 3,747,755 | A | | 7/1973 | Senturia et al. | 209/111.5 |
| 3,800,936 | A | | 4/1974 | Anfossi | |
| 3,908,814 | A | | 9/1975 | Hieronymus | 198/34 |
| 4,069,145 | A | | 1/1978 | Sommer, Jr. et al. | 209/212 |
| 4,093,062 | A | | 6/1978 | Sjögren | |
| 4,094,772 | A | | 6/1978 | Hillekamp et al. | 209/12 |
| 4,102,056 | A | | 7/1978 | Angelo et al. | |
| 4,124,168 | A | | 11/1978 | Bialski et al. | 241/14 |
| 4,131,540 | A | | 12/1978 | Husome et al. | |
| 4,176,750 | A | | 12/1979 | Holmes | |
| 4,207,177 | A | | 6/1980 | Block | 209/44.2 |
| 4,225,427 | A | | 9/1980 | Schnell | 209/44.1 |
| 4,231,526 | A | | 11/1980 | Ortner et al. | 241/28 |
| 4,352,430 | A | | 10/1982 | Maier et al. | |
| 4,440,284 | A | | 4/1984 | DeWoolfson | 194/4 R |
| 4,505,371 | A | | 3/1985 | Krueger et al. | |
| 4,533,053 | A | | 8/1985 | Kenny et al. | 209/636 |
| 4,533,054 | A | | 8/1985 | Sommer, Jr. et al. | 209/687 |
| 4,541,530 | A | | 9/1985 | Kenny et al. | 209/571 |
| 4,542,689 | A | | 9/1985 | Trolle | 100/215 |
| 4,609,108 | A | | 9/1986 | Hristozov et al. | |
| 4,632,320 | A | | 12/1986 | Holz et al. | 241/46.17 |
| 4,657,144 | A | | 4/1987 | Martin et al. | |
| 4,686,371 | A | * | 8/1987 | Birch et al. | 250/461.1 |
| 4,699,510 | A | * | 10/1987 | Alguard | 250/461.1 |
| 4,718,558 | A | | 1/1988 | Castaneda | |
| 4,718,559 | A | | 1/1988 | Kenny et al. | 209/571 |
| 4,741,042 | A | | 4/1988 | Throop et al. | 382/1 |
| 4,760,925 | A | | 8/1988 | Stehle et al. | 209/616 |
| 4,830,501 | A | | 5/1989 | Terashita | 356/402 |
| 4,844,351 | A | | 7/1989 | Holloway | 241/19 |
| 4,909,930 | A | | 3/1990 | Cole | |
| 4,919,534 | A | | 4/1990 | Reed | |
| 4,929,342 | A | | 5/1990 | Johnston | 209/12 |
| 4,945,253 | A | | 7/1990 | Frohardt | |
| 5,022,644 | A | | 6/1991 | Burge | |
| 5,024,335 | A | | 6/1991 | Lundell | 209/618 |
| 5,048,674 | A | | 9/1991 | Wilbur et al. | |
| 5,060,870 | A | | 10/1991 | Trezek et al. | 241/19 |
| 5,085,325 | A | | 2/1992 | Jones et al. | |
| 5,091,077 | A | | 2/1992 | Williams | 209/12 |
| 5,092,526 | A | | 3/1992 | Takata | |
| 5,100,005 | A | | 3/1992 | Noble et al. | 209/583 |
| 5,100,537 | A | | 3/1992 | Krause | 209/2 |
| 5,101,977 | A | | 4/1992 | Roman | 209/3 |
| 5,111,927 | A | | 5/1992 | Schulze, Jr. | 194/209 |
| 5,115,144 | A | | 5/1992 | Konishi et al. | |
| 5,115,987 | A | | 5/1992 | Mithal | 241/23 |
| 5,134,291 | A | | 7/1992 | Ruhl, Jr. et al. | |
| 5,139,339 | A | | 8/1992 | Courtney et al. | |
| 5,143,308 | A | | 9/1992 | Hally et al. | 241/76 |
| 5,150,307 | A | | 9/1992 | McCourt et al. | |
| 5,165,676 | A | | 11/1992 | Blessing et al. | 271/273 |
| 5,169,588 | A | | 12/1992 | Estepp | 264/331.17 |
| 5,183,251 | A | | 2/1993 | Sardella | |
| 5,190,165 | A | | 3/1993 | Garfield, Jr. | 209/655 |
| 5,197,678 | A | | 3/1993 | Trezek et al. | 241/21 |
| 5,201,921 | A | | 4/1993 | Luttermann et al. | 8/506 |
| 5,209,355 | A | | 5/1993 | Mindermann | 209/3.1 |
| 5,242,059 | A | | 9/1993 | Low et al. | |
| 5,257,577 | A | | 11/1993 | Clark | 100/99 |
| 5,260,576 | A | | 11/1993 | Sommer, Jr. et al. | |
| 5,297,667 | A | | 3/1994 | Hoffman et al. | 198/492 |
| 5,299,693 | A | | 4/1994 | Ubaldi et al. | 209/3.3 |
| 5,301,816 | A | | 4/1994 | Weber et al. | 209/616 |
| 5,314,072 | A | | 5/1994 | Frankel et al. | 209/44.1 |
| 5,315,384 | A | | 5/1994 | Heffington et al. | |
| 5,318,172 | A | | 6/1994 | Kenny et al. | 209/524 |
| 5,318,173 | A | | 6/1994 | Datari | |
| 5,322,152 | A | | 6/1994 | Tommila et al. | 194/212 |
| 5,333,739 | A | | 8/1994 | Stelte | |
| 5,333,797 | A | | 8/1994 | Becker et al. | 241/19 |
| 5,335,791 | A | | 8/1994 | Eason | |
| 5,339,962 | A | | 8/1994 | Sommer, Jr. et al. | 209/576 |
| 5,339,963 | A | | 8/1994 | Tao | |
| 5,344,026 | A | | 9/1994 | Booth et al. | |
| 5,348,136 | A | | 9/1994 | Kenny et al. | 198/443 |
| 5,348,162 | A | | 9/1994 | Wroblewski | 209/35 |
| 5,361,913 | A | | 11/1994 | Melchionna | 209/583 |
| 5,398,818 | A | | 3/1995 | McGarvey | |
| 5,402,264 | A | | 3/1995 | Wilbur et al. | |
| 5,419,438 | A | | 5/1995 | Squyres et al. | |
| 5,419,498 | A | * | 5/1995 | Rasmussen et al. | 241/280 |
| 5,423,431 | A | | 6/1995 | Westin | |
| 5,440,127 | A | | 8/1995 | Squyres | |
| 5,443,164 | A | | 8/1995 | Walsh et al. | |
| 5,460,271 | A | | 10/1995 | Kenny et al. | 209/576 |
| 5,464,981 | A | | 11/1995 | Squyres et al. | |
| 5,469,973 | A | | 11/1995 | Booth et al. | |
| 5,481,864 | A | | 1/1996 | Wright | |
| 5,497,871 | A | | 3/1996 | Ciolkevich | 198/443 |
| 5,501,344 | A | | 3/1996 | Kaiser et al. | |
| 5,512,758 | A | * | 4/1996 | Kobayashi et al. | 250/461.1 |
| 5,520,290 | A | | 5/1996 | Kumar et al. | |
| 5,531,331 | A | | 7/1996 | Barnett | |
| 5,533,628 | A | | 7/1996 | Tao | |
| 5,555,984 | A | | 9/1996 | Sommer, Jr. et al. | |
| 5,581,353 | A | | 12/1996 | Taylor | |
| 5,615,778 | A | | 4/1997 | Kaiser et al. | |
| 5,632,381 | A | | 5/1997 | Thust et al. | |
| 5,675,416 | A | | 10/1997 | Campbell et al. | |
| 5,676,256 | A | | 10/1997 | Kumar et al. | |
| 5,689,757 | A | | 11/1997 | Ferrante et al. | |
| 5,695,035 | A | | 12/1997 | Fukushima et al. | |
| 5,703,784 | A | | 12/1997 | Pearson | 364/478.11 |
| 5,770,864 | A | | 6/1998 | Dlugos | |
| 5,789,741 | A | | 8/1998 | Kinter et al. | |
| 5,794,788 | A | | 8/1998 | Massen | |
| 5,797,327 | A | | 8/1998 | Gieser et al. | |
| 5,799,105 | A | | 8/1998 | Tao | |
| 5,799,801 | A | | 9/1998 | Clark et al. | 209/667 |
| 5,813,542 | A | | 9/1998 | Cohn | |
| 5,813,543 | A | | 9/1998 | Gesing et al. | |
| 5,848,706 | A | | 12/1998 | Harris | |
| 5,861,919 | A | | 1/1999 | Perkins et al. | |
| 5,862,919 | A | | 1/1999 | Eason | |
| 5,884,775 | A | | 3/1999 | Campbell | |
| 5,900,943 | A | | 5/1999 | Owen | 356/406 |
| 5,901,856 | A | | 5/1999 | Brantley, Jr. et al. | 209/672 |
| 5,917,585 | A | | 6/1999 | Roe et al. | 356/73 |
| 5,954,206 | A | | 9/1999 | Mallon et al. | |
| 5,955,741 | A | | 9/1999 | Kayani | |
| 5,960,964 | A | | 10/1999 | Austin et al. | 209/672 |
| 5,966,217 | A | | 10/1999 | Roe et al. | |
| 5,979,240 | A | | 11/1999 | Rix et al. | |
| 6,022,017 | A | | 2/2000 | Cummings et al. | |
| 6,060,677 | A | | 5/2000 | Ulrichsen et al. | |
| 6,064,056 | A | | 5/2000 | Doak | 250/223 |
| 6,068,106 | A | | 5/2000 | Brizzi et al. | |

| | | | | |
|---|---|---|---|---|
| 6,076,684 | A | 6/2000 | Bollegraaf | 209/668 |
| 6,137,074 | A | 10/2000 | Doak | 209/581 |
| 6,263,291 | B1 | 7/2001 | Shakespeare et al. | 702/85 |
| 6,303,925 | B1 * | 10/2001 | Edmonds | 250/223 R |
| 6,335,501 | B1 | 1/2002 | Khalfan | 209/582 |
| 6,353,197 | B1 | 3/2002 | Ulrichsen et al. | |
| 6,369,882 | B1 | 4/2002 | Bruner et al. | 356/73 |
| 6,373,575 | B1 | 4/2002 | Takayama et al. | 356/445 |
| 6,509,537 | B1 | 1/2003 | Krieg et al. | |
| 6,778,276 | B2 | 8/2004 | Bruner et al. | |
| 7,262,380 | B1 | 8/2007 | Ulrichsen et al. | |
| 2002/0017445 | A1 | 2/2002 | Mukai | |

FOREIGN PATENT DOCUMENTS

| | | | |
|---|---|---|---|
| CA | 2235665 | | 10/1998 |
| DE | 3615644A 1 | | 11/1987 |
| DE | 3828067 | A1 | 3/1990 |
| DE | 3926641 | A1 | 2/1991 |
| DE | 3926641 | | 2/1991 |
| DE | 4125045 | A1 | 2/1993 |
| DE | 4135394 | A1 | 4/1993 |
| DE | 4305006 | A1 | 9/1993 |
| DE | 44 17 357 | A1 | 11/1995 |
| DE | PCT/DE95/00966 | | 11/1995 |
| DE | 4241990 | C2 | 2/1997 |
| EP | 291 959 | A2 | 11/1988 |
| EP | 0484221 | A2 | 5/1992 |
| EP | 0873797 | A2 * | 10/1998 |
| EP | 873797 | | 10/1998 |
| JP | 9314070 | A | 12/1997 |
| JP | 11-084745 | | 3/1999 |
| RU | 1411228 | | 7/1988 |
| SU | 1050992 | | 10/1983 |
| WO | WO 96/06690 | | 3/1996 |

OTHER PUBLICATIONS

Exhibit B: U.S. Appl. No. 11/325,835, filed Jan. 5, 2006 (now U.S. Patent No. 7,173,709) and its file history.

Exhibit C: U.S. Appl. No. 11/514,449, filed Sep. 1, 2006 (now U.S. Patent No. 7,499,172) and its file history.

Exhibit D: U.S. Appl. No. 12/252,909, filed Oct. 16, 2008 (still pending) and its file history.

U.S. Appl. No. 09/301,715, filed Apr. 29, 1999, and issued as U.S. Patent No. 6,369,882 on Apr. 9, 2002.

U.S. Appl. No. 10/428,311, filed May 2, 2003, and issued as U.S. Patent No. 6,778,276 on Aug. 17, 2004.

PCT Patent Application No. US/00/11761, filed Apr. 28, 2000.

Catalog of Magnetic Separation Systems, Inc. entitled "Systems for Separation and Sensing"(undated).

Brochure entitled "MSS Pen Binary Bottlesort®" (Undated).

Brochure entitled "MSS Plasticsort™" (Undated).

Brochure entitled "Machinefabriek Lubo® Mobile Systems" (Undated) discloses a screening unit having rotating disc on parallel shafts.

Brochure entitled "Machinefabriek Lubo® Projects" (Undated) discloses a screening unit having rotating disc on parallel shafts.

* cited by examiner

METHOD OF SORTING WASTE PAPER

Matter enclosed in heavy brackets [ ] appears in the original patent but forms no part of this reissue specification; matter printed in italics indicates the additions made by reissue.

This application is a continuation of our pending application Ser. No. 09/301,715 filed Apr. 29, 1999, now U.S. Pat. No. 6,369,882 B1.

Be it known that I, Russell S. Bruner, a citizen of the United States residing at 726 Poplar Avenue, Mt. Juliet, Tenn. 37122 and I, David R. Morgan, a citizen of the United Slates residing at 9921 U.S. Highway 68 East, Benton, Ky. 42025, and I, Garry R. Kenny, a citizen of the United States residing at 6299 McDaniel Rd., College Grove, Tenn. 37046, *and I, Paul G. Gaddis, a citizen of the United States residing at 2000 Alaska Way #156, Seattle, Wash. 98121, and I, David Lee, a citizen of the United States residing at 3614 North 30th Street, Tacoma, Wash. 98407, and I, James M. Roggow, a citizen of the United States residing at 14526 26th Avenue, Court East, Puyallup, Wash. 98374,* have invented a new and useful [“System and Method For Sensing White Paper.”] *“Method of Sorting Waste Paper.”*

BACKGROUND OF THE INVENTION

The present invention relates to a system and method for sorting mass recyclables and more particularly to a system for sensing and sorting white paper from other objects.

It will be appreciated by those skilled in the art that society desires to recycle as much of its waste materials as possible. For example, aluminum cans, plastic bottles, and other items have been the source of mixed recyclable efforts in the past. The assignee of the present application, Magnetic Separation Systems, Inc. (MSS) is a world leader in mixed recyclables. MSS is also the owner of many patents disclosing technologies for sorting and concentrating aluminum and sorting plastics.

One other type of mixed recyclable is paper. In the past, recyclable efforts have been dominated by hand sorting of paper by type. One common effort is curbside recycling. Other efforts have been to sort paper from other types of materials. Unfortunately, as with any other procedure, any type of hand sorting requires an intensive use of labor that is not always efficient.

What is needed, then, is a method and system that can sort white paper from a stream of other paper. This needed system must also be capable of sorting a stream of material from white paper in case the stream is dominated by materials other than white paper. The system must decrease the amount of labor presently being used. The system must be economical. The system must be effective. The system is presently lacking in prior art.

SUMMARY OF THE INVENTION

*The present invention discloses a method of sorting waste paper, comprising spreading waste paper out into a layer that is substantially one unit thick; detecting the presence or absence of a predetermined optical characteristic as the layer of paper is passed by a sensor; and controlling one or more actuators that direct a sheet of paper based on the presence or absence of the predetermined optical characteristic.*

The present invention discloses a system and method for sorting white paper, and especially a type of white paper commonly referred to as bright white paper, from other objects. One reason that recycling of bright white paper is very desirable is that the fluorescent chemicals added to such papers are expensive plus the bright white paper tends to be a very high quality paper fiber. Thus, this is a premium paper fraction for recycling. The system may also sort other objects from white paper.

The present invention uses an energy source that is preferably an ultraviolet light light that is concentrated in some manner onto an object. The energy is focused on the paper. If the paper is bright white paper, the ultraviolet radiation will cause the brightening agents in the white paper to fluorescence into an energy having a different and longer wavelength. The fluorescence is then measured.

The system and method of the present invention is particularly adapted for use in sensing the presence of bright white paper that flows past the sensor on a conveyor. The conveyor is constantly illuminated with the ultraviolet light. Also, a second light source is provided which periodically illuminates an inspection zone of the conveyor with a second light which is in the visible light spectrum, and preferably in the blue-green portion of the visible light spectrum.

A sensor located above the inspection zone of the conveyor collects light from the inspection zone of the conveyor. The collected light includes both emitted fluorescence from bright white paper located in the inspection zone and reflected light from the second light source reflected off of objects in the inspection zone.

Periodically, the sensing system senses first and second parameters of the light collected from the inspection zone. The first parameter is the level of reflection of the second light source in order to determine whether any object is present on the conveyor in the inspection zone. The second parameter sensed is the level of fluorescent light to determine whether an object present in the inspection zone is bright white paper.

Thus, if the sensed level of the reflected light from the second light source is below a certain threshold, the system will determine that no object is present in the inspection zone on the conveyor. If the sensed level of reflected light from the second light source is above a threshold level, the system will sense that some object is present in the inspection zone on the conveyor, but the identification of that object will depend upon the sensed level of fluorescent energy coming from that object. If the sensed level of fluorescent energy from the object is below a threshold level, the system will determine that the object is something other than bright white paper. If the sensed level of fluorescent energy is above a predetermined threshold, the system will determine that the sensed object is bright white paper.

The system may then send control signals to an ejection means which will eject either the bright white paper fraction or the non-bright white paper fraction from the paper stream flowing across the conveyor.

Accordingly one object of the present invention is to provide a system and method for sensing and sorting bright white paper from other objects.

Another object of the present invention is to provide a system that allows someone to sort bright white paper from other objects that is not labor intensive.

Another object of the present invention is to provide a system that can sort both bright white paper from other objects and other objects from bright white paper.

Still a further object of the present invention is to provide an accurate system for sensing bright white paper.

*And another object of the present invention is to provide improved methods of sorting waste paper.*

Other and further objects features and advantages of the present invention will be readily apparent to those skilled in the art upon a reading of the following disclosure when taken in conjunction with the accompanying drawings.

BRIEF DESCRIPTION OF THE DRAWINGS

FIG. 5b is an elevation view of the lens of FIG. 5a.

FIG. 6b is an elevation sectioned view of the sensor housing, taken along line 6b—6b of FIG. 6a. FIG. 6b shows the cavity in which the lens is received.

FIG. 6c is another elevation sectioned view through the sensor housing, taken along line 6c—6c of FIG. 6a. FIG. 6c illustrates cavities in which the second light source elements are placed.

DESCRIPTION OF THE PREFERRED EMBODIMENTS

Figure 1:
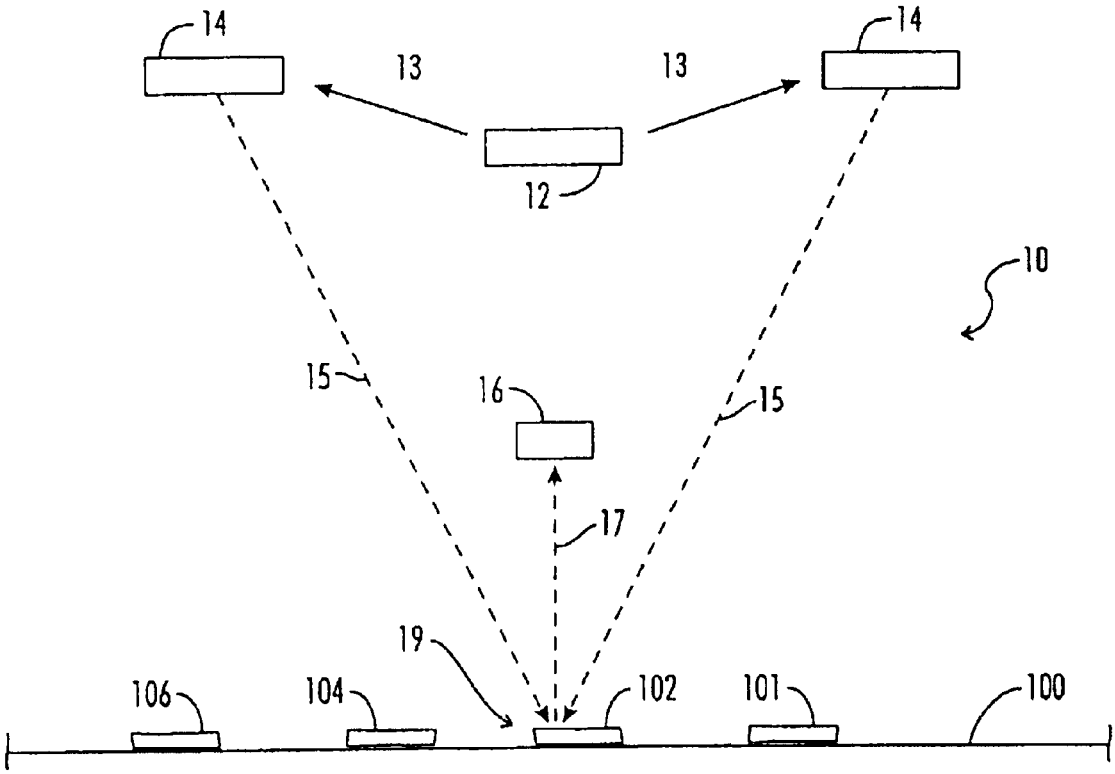
FIG. 1 is a block diagram of the system and method of the present invention.

Referring now the drawings, and particularly to FIG. 1, the system of the present invention is shown and generally designated by the numeral 10. The system 10 includes a first light source 12 which preferably is an ultraviolet light source 12. Ultraviolet light energy emitted from source 12 travels along paths 13 to a concentrator means 14 which then directs the light along paths 15 so as to focus the ultraviolet light energy on an inspection zone or focal zone 19 on a conveyor 100 located below the apparatus 10. A portion of any light energy reflected from or emitted from any objects within the inspection zone 19 will travel upward as indicated by path 17 to a sensor 16. If an object such as 102 is located in the inspection zone 19, the light reflected from and/or emitted from the object 102 in inspection zone 109 and received by sensor 16 can be examined to determine the nature of the object 102, and particularly to determine whether the object 102 is bright white paper. Other objects 101, 104 and 106 are also schematically illustrated in place upon the conveyor belt 100.

The system 10 is particularly designed to determine whether an object in the inspection zone 19 is bright white paper. Bright white paper is a common name for a type of high quality paper commonly used in offices for printers and copiers. Bright white paper is typically a high quality paper fiber which has been treated with brighteners which cause the paper to fluoresce in the presence of ultraviolet light. When ultraviolet light energy falls upon bright white paper, the brighteners in the object will fluoresce and will emit light energy having a wavelength in the range of from about 400 to about 550 nanometers, which is in the visible light spectrum. The fluorescent energy emitted from bright white paper when an ultraviolet light is shown on it is great when compared to the amount of fluorescent energy that will be emitted from objects other than bright white paper.

Figure 3:
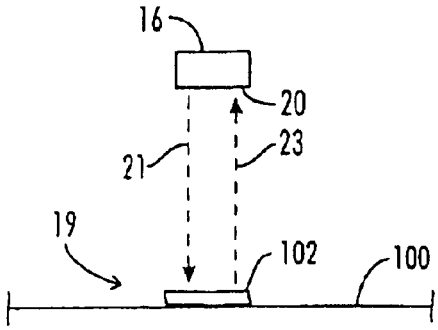
FIG. 3 is a block diagram of the secondary light source of the present invention.

FIG. 3 schematically illustrates a second feature of the system 10 which includes a second light source 20. As will be further described below, the second light source 20 is contained within a common housing with the sensor 16. The second light source 20 is preferably a source of visible light energy. One preferred second light source 20 is a blue light emitting diode which emits light energy having a wavelength of approximately 480 nanometers. Light from the second light source 20 travels downward along path 21 and is reflected off an object such as object 102 located within the inspection zone 19. The reflected light energy travels back upward along path 23 where it is also received by the sensor 16.

As will be further described below, the general purpose of the second light source 20 is to provide a means for detecting whether any object is present on the conveyor belt 100 within the inspection zone 19. The sensor 16 and its associated control apparatus will be calibrated so that when the reflected light 23 exceeds a certain threshold, it will provide a determination that some object other than the black conveyor belt 100 is located within the inspection zone 19. A second determination will then be made as to the level of fluorescent energy traveling upward along path 17 to the sensor 16. If an object is present in the inspection zone 19, but the level of fluorescent energy is below a predetermined threshold, the system 10 will determine that the object is not the desired bright white paper. On the other hand, if an object is determined to be present, and the amount of fluorescent energy 17 emitted by that object is above the predetermined threshold, the system 10 will determine that the object is bright white paper.

Figure 10:
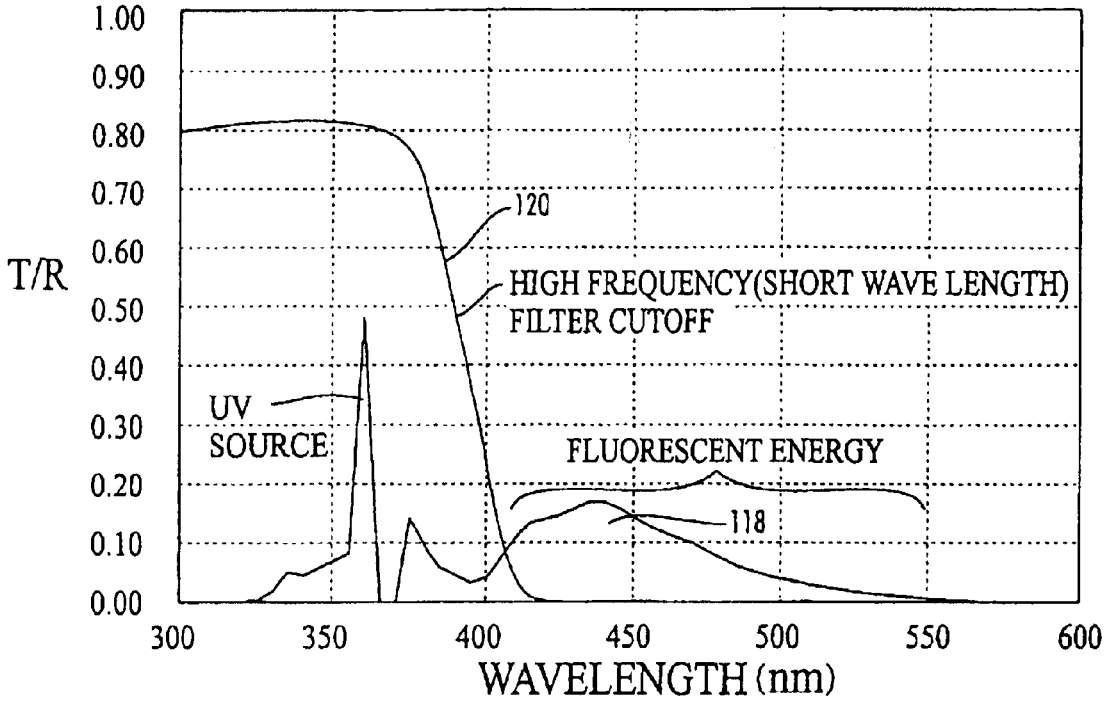
FIG. 10 is a graph illustrating the wavelength of the ultraviolet energy source and of the emitted fluorescent energy from bright white paper. Also shown is a high frequency cut-off of a filter.

FIG. 10 is a graphical illustration of the electromagnetic radiation energy which might be picked up by sensor 16. The horizontal axis represents the wavelength of the electromagnetic radiation, and the vertical axis represents the relative intensity of radiation.

There is a peak at approximately 360 nanometers in FIG. 10 which represents the frequency of the ultraviolet light energy radiating from source 12. To the extent that ultraviolet energy is merely reflected off of the focal zone 19 and received by sensor 16, it would create a spike as shown in FIG. 10.

As previously noted, when ultraviolet light energy falls upon a piece of bright white paper containing fluorescing additives, the additives fluoresce, thus converting some of the ultraviolet light energy into visible light energy having a longer wavelength (and thus lower frequency). In FIG. 10, a hump in the detected energy generally designated at 118 is representative of the fluorescent energy emitted from a piece of bright white paper. As is apparent in FIG. 10, the hump 118 begins at a wavelength of approximately 400 nanometers, peaks at about 440 nanometers, then drops off and is essentially absent at about 550 nanometers wavelength.

In order to isolate the fluorescent energy emitted from bright white paper, the sensor 16 preferably has a filtering means associated therewith. Preferably the filtering means is a band pass filter which will allow light energy only within the range of from 400 to 500 nanometers length to pass therethrough. The details of construction of this filtering means are further described below. In FIG. 10, the high frequency, and thus short wavelength, cut off of the filter is indicated by the curve 120. Since this high frequency cut off is at a lower frequency than the ultraviolet light source, reflected ultraviolet light energy will not be sensed by sensor 16.

The secondary light source 20 previously described operates at a wavelength of 480 nanometers, so that when the secondary light source reflects off of an object within the inspection zone 19 that reflected light 23 can pass through the filter means.

Figure 7:
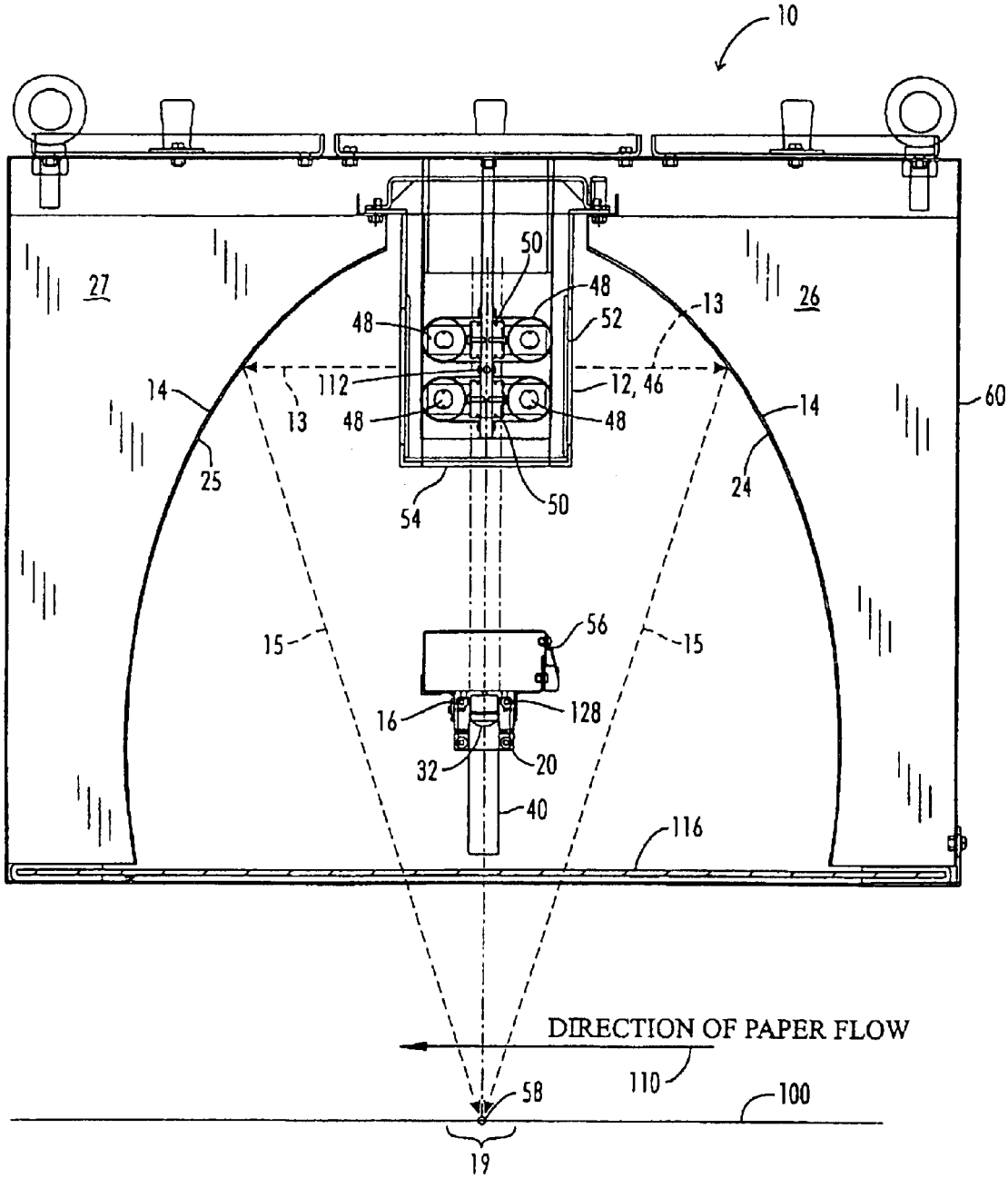
FIG. 7 is an elevation view of the sensor of the present invention as viewed from the side of the conveyor.

FIG. 7 is an elevation sectioned view of the sensing system 10 in place over the conveyor 100.

The first light source 12 is a light module 46 which includes four parallel elongated tubular ultraviolet light bulbs 48 which are seen in cross-section in FIG. 7. The light bulbs 48 extend transversally across the width of the conveyor 100 perpendicular to the direction of paper flow indicated by the arrow 110. The bulbs 48 are contained within a housing 52. Electronic starters 50 are associated with the bulbs 48 and cause the same to turn on and off when electrical power is directed thereto in a well known manner. A glass panel 54 covers the lower side of module 46.

Thus, most of the ultraviolet light energy from bulbs 48 is emitted laterally as along the paths 13 previously noted, where it falls upon the concentrators 14. The concentrators 14 are preferably curved reflectors formed in the shape of an arc of an ellipse so that all light falling thereon will be reflected toward a focal point 58 lying in the center of the inspection zone 19 on the conveyor 100. The ultraviolet light energy reflected from concentrators 14 follows paths generally designated as 15 to the focal point 58.

Figure 2:
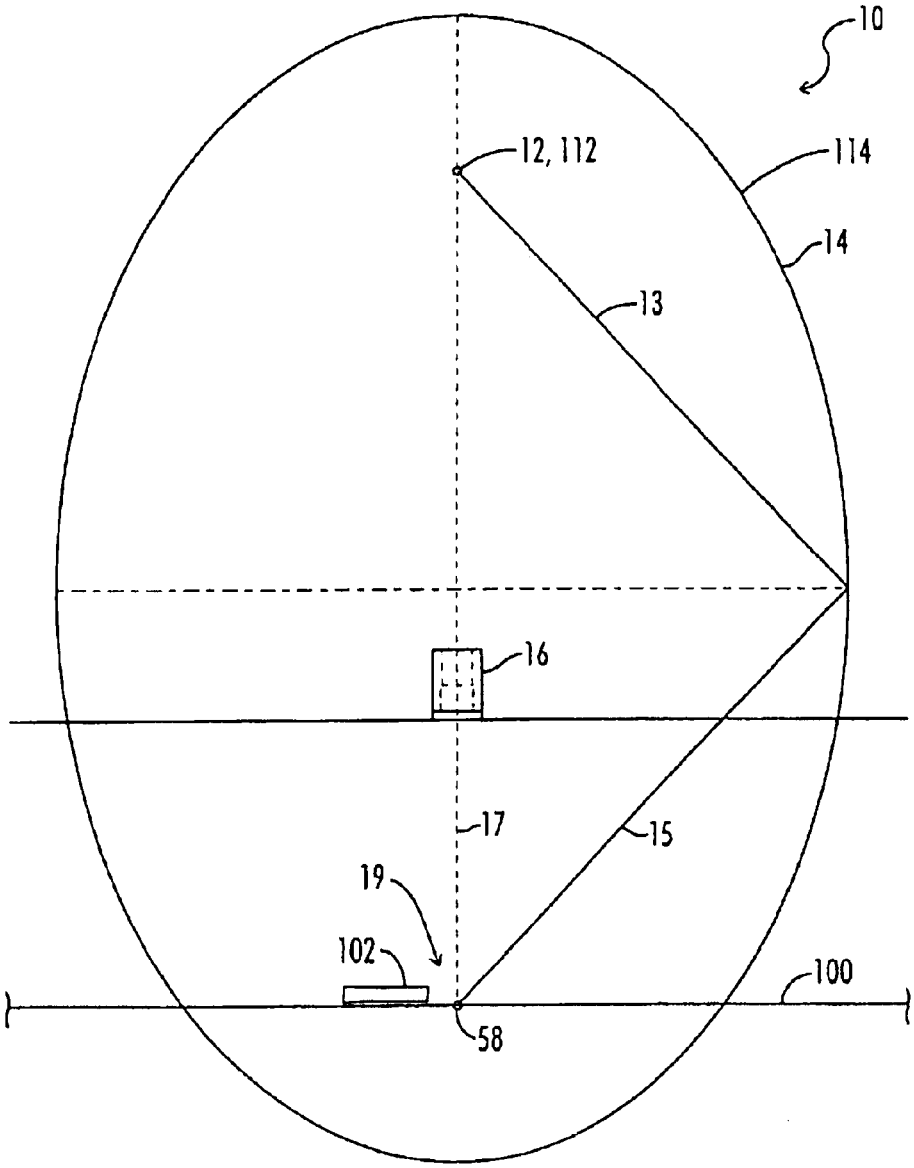
FIG. 2 is an optical diagram of the system and method of the present invention.

The geometric layout of the concentrator 14 is best illustrated in the schematic representation shown in FIG. 2. As indicated in FIG. 2, the light source 12 has a central point 112 which is generally coincident with the upper focal point 112 of an ellipse 114 upon which the reflecting walls of concentrator 14 lie. The lower focal point 58 of the ellipse 114 falls upon the conveyor 100 in the center of the inspection zone 19.

Figure 4:
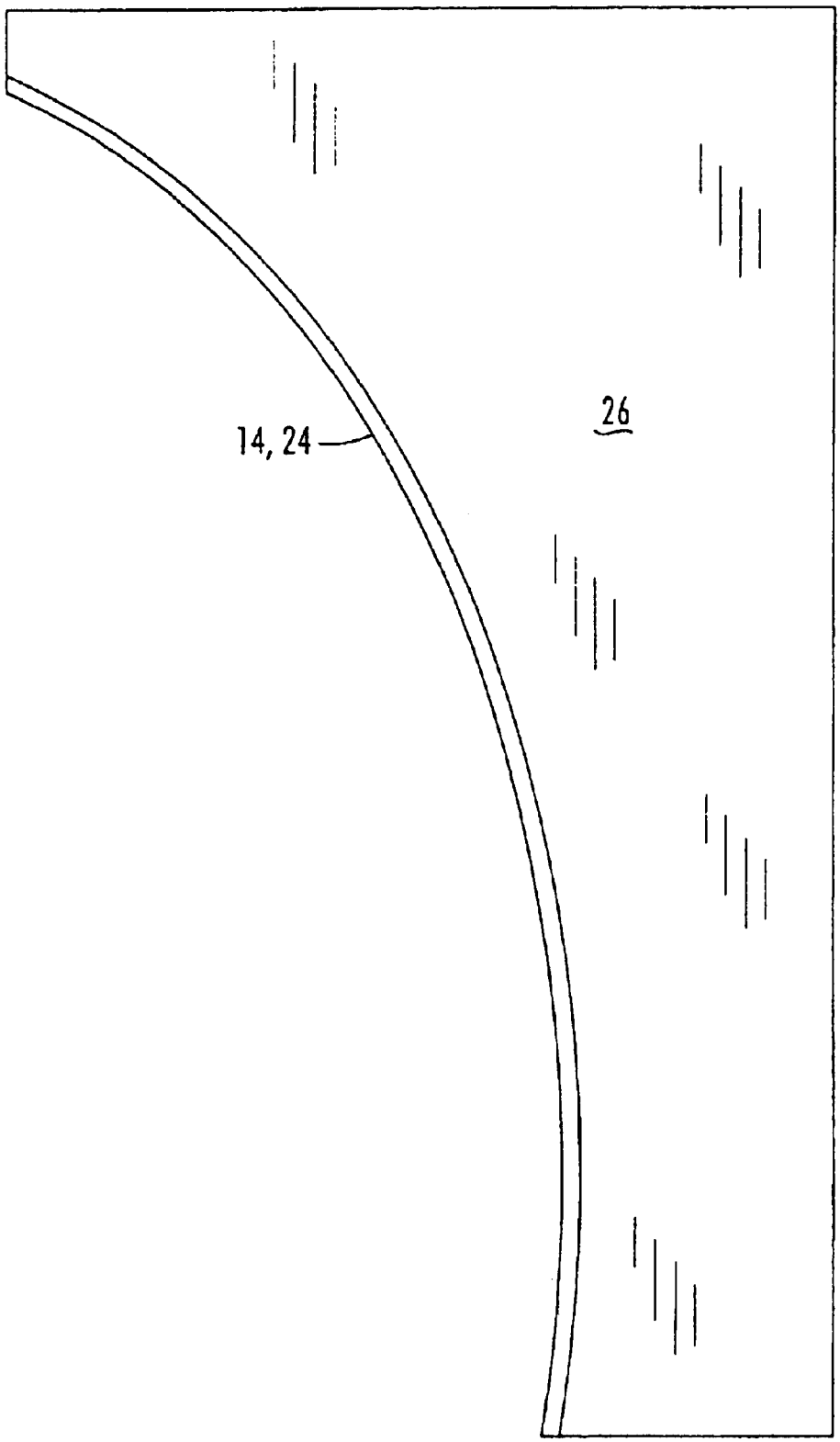
FIG. 4 is an elevation view of one half of the reflector of the present invention as viewed from the side of the conveyor.

Referring now to FIGS. 4 and 7, the concentrator 14 is constructed from first and second reflecting walls 24 and 25 which are supported within a housing 60 of the apparatus 10 by a plurality of brackets such as 26 and 27. The reflector walls 24 and 25 are preferably polished stainless steel. The brackets such as bracket 26 shown in FIG. 4 may also be manufactured from stainless steel.

The lower end of the housing 60 of apparatus 10 is closed by a transparent glass shield 116 which allows the light energy to pass therethrough while preventing dirt, paper and debris from entering the apparatus 10.

The reflecting walls 24 and 25 may be generally described as an elliptical reflecting lens having focal point 58 within the inspection zone 19.

Figure 6A:
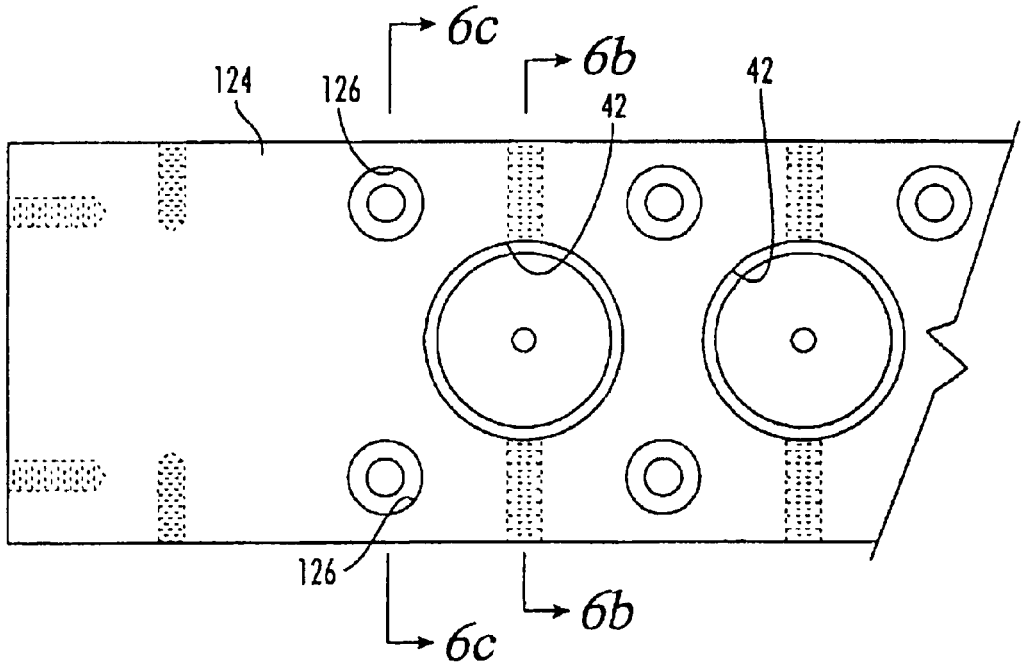
FIG. 6a is a bottom view of a sensor housing, showing the layout of an array of lens cavities and cavities for receiving the second light sources.
Figure 6B:
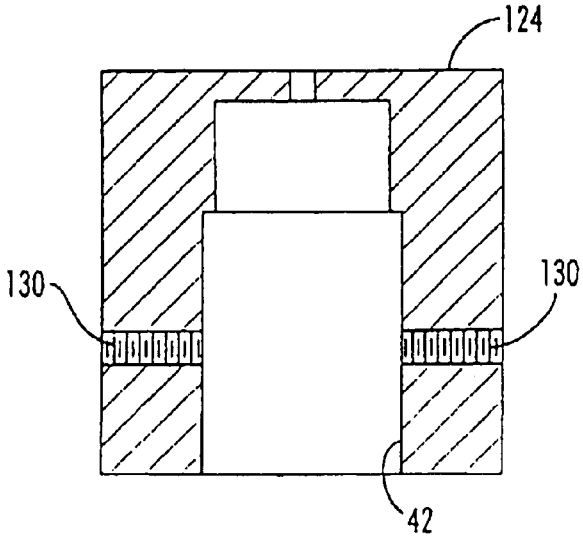
Figure 6C:
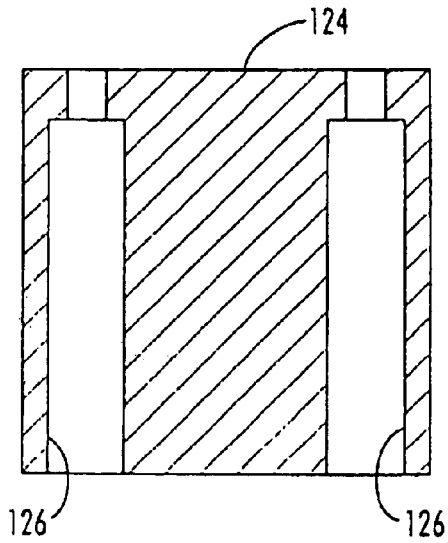

Referring now to FIGS. 6a, 6b and 6c, a sensor housing or lens housing is shown and generally designated by the numeral 124. The sensor housing 124 is an elongated housing which lies across the width of the conveyor 100 and can be described as being transverse to and is perpendicular to the direction of travel 110 along the conveyor belt 100.

The sensor housing 124 has a plurality of lens cavities 42 and a plurality of secondary light source cavities 126 defined therein. An array of sensor elements are carried by housing 124.

FIG. 6b is a sectioned view taken along lines 6b—6b of FIG. 6a, showing the details of construction of one of the lens cavities 42.

FIG. 6c is a sectioned view taken along lines 6c—6c of FIG. 6a, showing the details of construction of two secondary light source cavities 126.

The sensor housing is held in place by a bracket 56 as shown in FIG. 7.

Figure 5A:
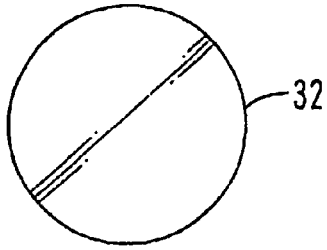
FIG. 5a is a plan view of a lens of a sensor element.
Figure 5B:
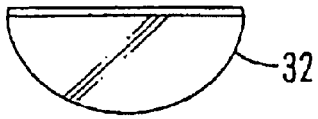
Figure 5C:
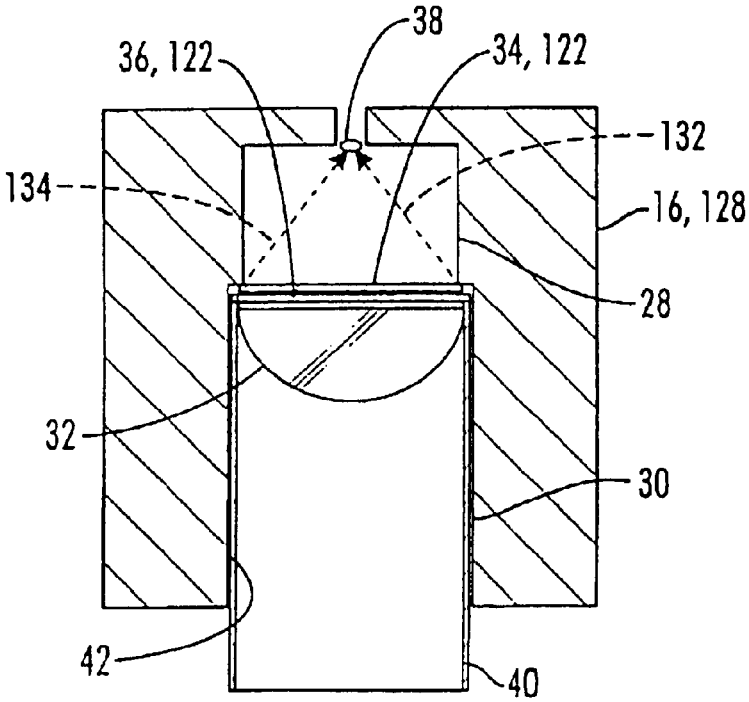
FIG. 5c is a schematic elevation partly sectioned view of a sensing element showing the lens in place within a collimator tube which, in turn, is in place within a lens housing.

Turning now to FIGS. 5a–5c, the details of construction of one of the sensing elements of sensor 16 will be described.

FIG. 5c is a schematic elevation cross-section view similar to FIG. 6b and schematically illustrating the components of one sensing element 128 of sensor 16. Each sensing element such as 128 is associated with one of the lens cavities 42.

A collimator tube 40 is received in each lens cavity 42 and held in place therein by set screws received through threaded holes 130 (See FIG. 6b). In one preferred embodiment each collimator tube is approximately 4" long, 1" outside diameter and ¾" inside diameter. The collimator tube 40 may be an aluminum tube having a matte black finish. The collimator tube 40 ensures that the light being collected by the sensing element 128 is substantially only light traveling directly upward from an object immediately below sensing element 128 in the focal zone 19.

Located at the upper end of each collimator tube 40 is a semi-spherical lens 32. Plan and side elevation views of one lens 32 are shown in FIGS. 5a and 5b, respectively.

Located immediately above the lens 32 is the filtering means 122 which includes first and second optical filter plates 34 and 36. The first optical filter plate is a high frequency pass filter 34, and the second optical filter plate 36 is a low frequency pass plate 36. As will be understood by those skilled in the art, the filter plates 34 and 36 can be selected to determine the frequencies of light energy which really will not pass therethrough. Filter plates 34 and 36 are standard optical filters which are available from Edmund Scientific.

The light energy which passes through the lens 32 is focused within a cone having outer boundaries along the dashed arrows 132 and 134 which focuses that energy upon a photo electric detector 38. The photo electric detector 38 is a silicone photo diode.

Thus, the band pass filter means 122 will pass fluorescent energy having a wavelength longer than a lower limit of about 400 nanometers, which lower limit is longer than the wavelength of the ultraviolet light from source 12. The filtering means 122 will further block fluorescent energy having a wavelength longer than an upper limit, which in the illustrated embodiment is preferably about 500 nanometers. The range of light energy having wavelength from 400 to 500 nanometers can be described as being in the blue-green portion of the visible light spectrum.

As previously noted, the light emitted from second light source 20 has a wavelength of approximately 480 nanometers, which will be passed by the filtering means 122 when said light is reflected from an object in the inspection zone 19.

Figure 9:
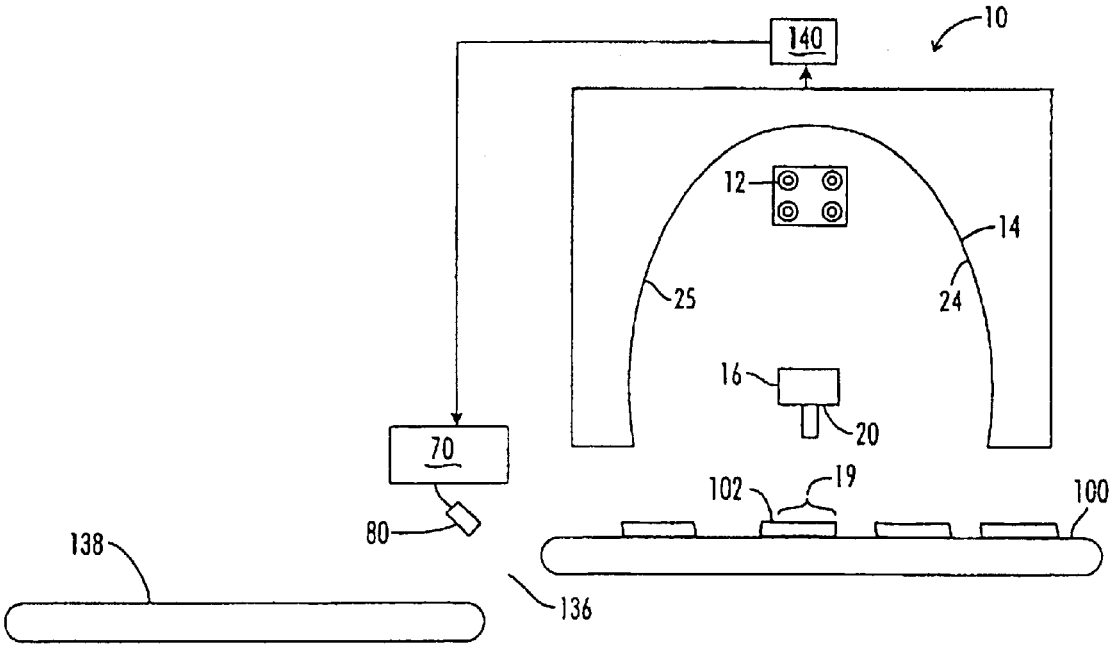
FIG. 9 is a schematic side elevation view of the sensor in place above a conveyor, and also shows an associated ejection system for ejecting a fraction of the flowing paper stream in response to signals from the sensor.

Referring now to FIG. 9, a general layout of the system 10 and associated conveyor apparatus is shown, whereby the sensor system 10 may be utilized to detect bright white paper on the conveyor 100 and to send control signals to an ejector mechanism 70 which uses air jets 80 to eject paper from the conveyor 100.

The conveyor 100, ejector system 70 and associated apparatus are shown in detail in an application of Michael R. Grubbs et al, entitled PAPER SORTING SYSTEM, U.S. patent application Ser. No. 09/301,992, filed Apr. 29, 1999, now U.S. Pat. No. 6,250,472 issued Jun. 26, 2001, and assigned to the assignee of the present invention. The details of construction of the system shown in the Grubbs et al. patent are incorporated herein by reference as if the same were fully set forth herein.

Figure 8:
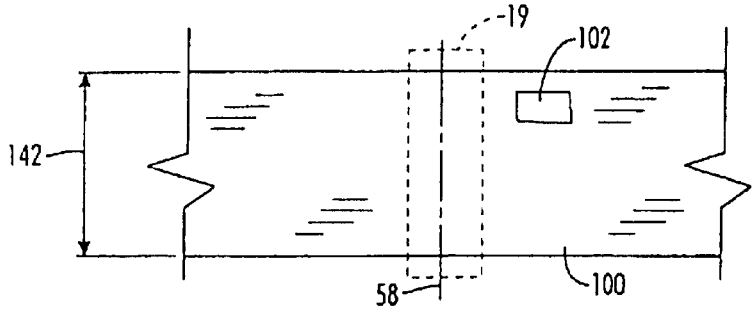
FIG. 8 is a schematic plan view of the conveyor showing the inspection zone.

FIG. 8 is a schematic plan view of the conveyor 100 illustrating an elongated strip shaped inspection zone 19 lying across a width 142 of the conveyor belt 100. The focal point 58 previously described with regard to the side elevation view of the ellipse is in fact a focal line 58 which defines the center line of the inspection zone 19.

In the system shown in FIG. 9 the first conveyor 100 conveys the paper objects 102 from right to left so that they pass under the sensor 16. The conveyor 100 is traveling at a very great rate of speed (as much as 1200 ft/min), and as the objects reach the left hand end of conveyor 100 they are launched off of the conveyor 100 and fly through the air across an ejection gap 136 toward a product conveyor 138.

Signals from the photo electric detector 38 are converted into digital signals which are directed to a microprocessor 140 which performs the measuring, sensing, comparing and evaluating functions. The microprocessor 140 will go through the evaluation steps described below, and at appropriate times will send a control signal to the ejector system 70 to direct compressed air to jet 80 so that the air jet 80 will be directed against an object which at that time is passing across the ejection gap 136. Any object impacted by an air jet as it crosses the gap 136 will be blown downward between the two conveyors 100 and 138 and will be part of an ejected paper stream fraction. Non-ejected paper will flow across the gap 136 and fall onto the conveyor 138 which will lake it to another location.

Figure 11:
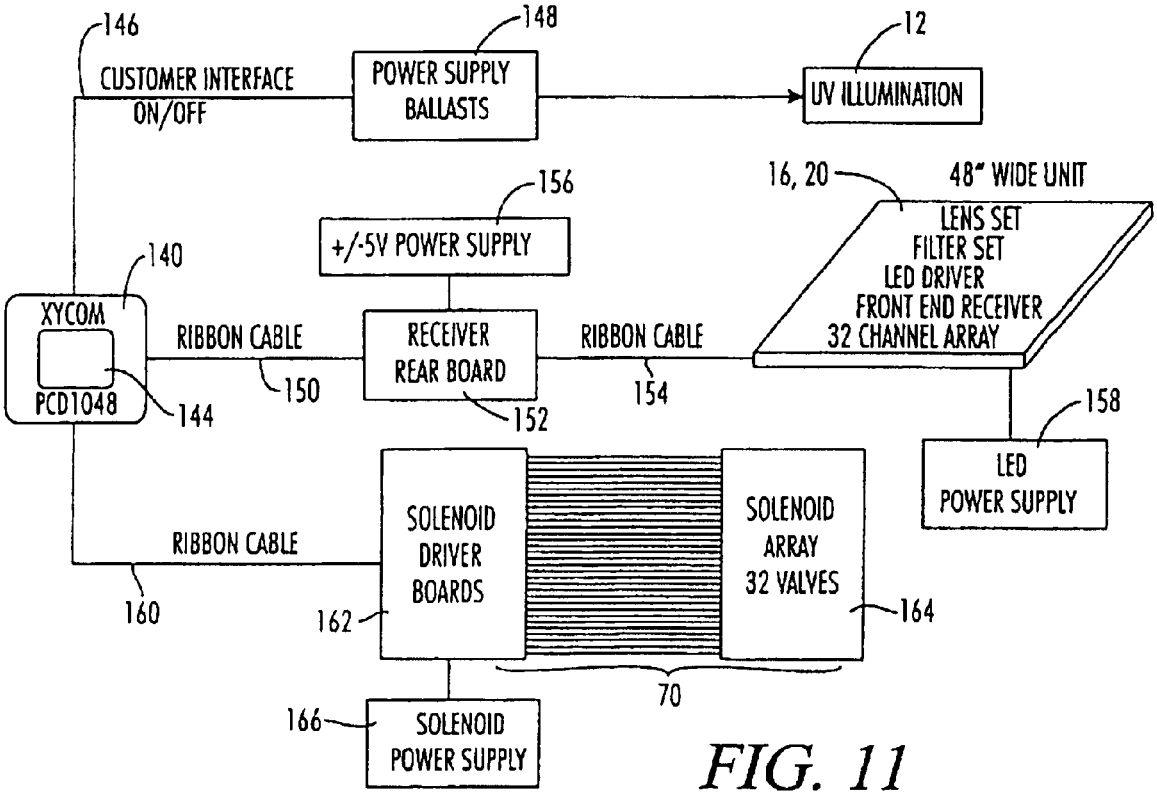
FIG. 11 is a block diagram of the electrical control system.

FIG. 11 is a schematic block diagram of the control system of the apparatus 10.

The microprocessor 140 may be a XYCOM model PCD1048 microprocessor available from XYCOM Automation, Inc. The microprocessor 140 preferably has touch screen operated control station 144 which allows system variables to be changed and the sort selection to be changed. The system provides the ability to perform a positive sort where non-bright white paper is ejected or a reverse sort where the bright white paper is ejected when the concentration of the targeted paper is less than that of the non-targeted paper.

The microprocessor 140 is connected by interface 146 to power supply ballasts 148 and then to the ultraviolet light source 12.

The microprocessor 140 is connected by a ribbon cable 150 to a rear receiver board 152 which is in turn connected by a ribbon cable 154 to the sensor unit 16 and the secondary light sources 20 contained in the sensor housing.

A power supply 156 is connected to the rear receiver board 152.

An LED power supply 158 is connected to the secondary light source 20.

The rear receiver board 152 includes amplifiers and analog to digital converters. Signals from the sensor 16 are communicated over cable 154 to the rear receiver board 152 where they are amplified and digitized before being passed over cable 150 to the microprocessor 140.

The microprocessor 140 also communicates over cable 160 to the ejector control system 70 which includes a plurality of solenoid driver boards 162 and an array of solenoid valves 164 which control the flow of air to the air jets 80. A solenoid power supply 166 is connected to the driver boards 162.

Methods of Operation

The methods of operation of the present invention will now be described with reference to FIGS. 7 and 9.

The system 10 provides an apparatus and method for sensing the presence of bright white paper on the conveyor 100 of the paper sorting system like that described in the Grubbs et al. application which has been incorporated herein by reference.

The conveyor 100 is directing a stream of waste paper from right to left as seen in FIG. 8 at a very high speed below the sensor 16.

The ultraviolet light source 12 is constantly on and constantly illuminates the inspection zone 19 on the conveyor belt 100 immediately below the sensor 16. As previously described, that ultraviolet light energy is focused on the inspection zone 19 by means of the elliptical shaped walls 24 and 25.

When a piece of paper such as 102 passes through the inspection zone 19, if the paper 102 is bright white paper, it will fluoresce and will re-radiate fluorescent light energy from the bright white paper. As previously described with reference to FIG. 1, a portion of that fluorescent energy will travel directly upward along the path 17 to the sensor 16.

Throughout this process, the inspection zone 19 will also be periodically illuminated with light from the second light source 20, which as previously noted is preferably a blue light emitting diode. In a preferred embodiment, the secondary light source 20 illuminates the inspection zone 19 every 3 milliseconds.

Light from the inspection zone 19, including both reflected light and emitted fluorescent light, is collected by the collimator tube 40 and passes through the lens 32 and the filtering means 122 to the photo electric detector 38. The photo electric detector 38 will convert the light energy into an electrical signal, which, in turn, is converted into a digital electric signal which is directed to the microprocessor 140.

A first measuring step or sensing step is performed by microprocessor 12 when the secondary light source 20 is on. This first sensed parameter will thus indicate the level of reflected light from secondary source 20, and if that level of reflected secondary light exceeds a predetermined threshold, the microprocessor 140 will determine that some object is present in the inspection zone 19 on the conveyor 100. Then, when the secondary light source 20 is off, the microprocessor 140 will perform a second measuring or sensing step while only the ultraviolet light illuminates the inspection zone 19. In this second step, the sensed light energy will be compared to the predetermined threshold for fluorescent energy, and if that threshold is exceeded, the microprocessor 140 will determine that an object present in the inspection zone 19 is bright white paper.

The microprocessor 140 can be described as periodically sensing first and second parameters of the light collected by the sensing element. The first parameter is the level of reflection from the inspection zone 19 of light originating with the secondary light source 20. If this first parameter exceeds a certain threshold, an indication is generated indicating that some object is present in the inspection zone 19 other than the conveyor belt 100 itself.

The second parameter sensed by the microprocessor 14 is the level of fluorescent light energy which has been radiated from an object within the inspection zone 19. If this level of fluorescent light energy exceeds a predetermined threshold, this will generate an indication that an object which is present in the inspection zone 19 is, in fact, bright white paper.

If the first parameter indicates that an object is present, but the second parameter indicates that the object is not bright white paper, then it is known that the object is one which should be separated from the bright white paper.

Depending upon the signals generated by the microprocessor 140, a control signal is then sent to the ejection system 70 to direct compressed air to air jets 80 to eject a selected fraction of the stream of paper which is moving along the conveyor 100. It will be appreciated that the microprocessor 140 can be programmed to either eject the bright white paper or to eject the non-bright white paper. Preferably, whichever type of paper comprises the smaller portion of the stream of paper flowing across conveyor 100 will be ejected, whereas the major portion will be allowed to flow across to the product conveyor 138.

The periodic illumination by secondary source 100 is preferably performed approximately every 3 milliseconds. In general, it may be described as being performed in excess of 100 times per second. Preferably the microprocessor 140 periodically senses the light being collected from the inspection zone 19 at the same periodic rate at which the secondary light source 20 is illuminating the inspection zone 19.

The paper objects will be traveling on the conveyor 100 at a speed of approximately 1200 feet per minute or 20 feet per second, thus by strobing every 3 milliseconds, a piece of letter size paper, 8½" wide would be strobed at least 10 times as it passed under the sensor 16.

The sensor 16 and associated microprocessor 140 can be described as an evaluating means for evaluating the level of fluorescent energy detected by each of the sensing elements to determine whether bright white paper is located below each sensing element.

As previously noted, there is preferably a linear array of sensing elements arranged across the width of the conveyor belt. For example, for a 48" wide conveyor, there may be 32 sensor elements. Signals from each of the sensing elements are separately analyzed, and control signals are separately sent to an array of 32 air jets 80, so that there is an ejection air jet 80 associated with each of the sensing elements. Thus, a paper object may be located toward one edge of the conveyor belt and its location will be determined by the identification of the sensing elements which sense the presence of that object therebelow. Then the associated air jets can be activated at the proper time to blow the sensed object through the ejection gap 136 if desired.

Thus, it is seen that the apparatus and methods of the present invention readily achieve the ends and advantages mentioned, as well as those inherent therein. While certain preferred embodiments of the invention have been illustrated and described for purposes of the present disclosure, numerous changes in the arrangement and construction of parts and steps may be made by those skilled in the art, which changes are encompassed within the scope and spirit of the present invention as defined by the appended claims.

What is claimed is:

1. A method of sorting waste paper, comprising:

spreading waste paper out into a layer that is substantially one unit thick;

detecting the presence or absence of a predetermined optical characteristic as the layer of paper is passed by a sensor; and controlling one or more actuators that direct a sheet of paper based on the presence or absence of the predetermined optical characteristic.

2. The method of claim 1, wherein the predetermined optical characteristic is fluorescence caused by optical brighteners in the paper, and wherein the presence or absence of the fluorescence is detected by:

applying ultraviolet light on a sheet of waste paper;

detecting light received from the paper in response to the ultraviolet light applied; and comparing the level of light received from the paper with a threshold to detect the presence or absence of optical brighteners in the paper.

*3. The method of claim 1, wherein:*

*said spreading step includes carrying said layer on a conveyor having a width; and*

*in said detecting step, said sensor includes an array of sensor elements spaced across the width of the conveyor.*

*4. The method of claim 3, wherein:*

*in said controlling step, said one or more actuators include one or more air jets.*

*5. The method of claim 4, wherein:*

*in said controlling step, said one or more air jets include an array of air jets spaced across the width of the conveyor, and said controlling step includes actuating an appropriate number of said air jets at an appropriate time to direct the sheet of paper.*

*6. The method of claim 5, wherein:*

*in said controlling step, each one of said air jets is associated with one of said sensing elements.*

*7. The method of claim 1, wherein:*

*in said controlling step, each of said actuators includes an air jet.*

*8. The method of claim 7, wherein:*

*said spreading step includes spreading said layer on a conveyor having a width; and*

*in said controlling step, said air jets comprise an array of air jets spaced across the width of the conveyor.*

*9. The method of claim 7, wherein:*

*said detecting step includes communicating sensor signals from the sensor to a microprocessor; and*

*said controlling step comprises communicating control signals from the microprocessor to an array of solenoid valves associated with the air jets and thereby controlling a flow of air to the air jets.*

*10. The method of claim 1, further comprising:*

*conveying the layer of waste paper on a first conveyor and launching the layer of waste paper off the first conveyor across a gap to a second conveyor; and*

*wherein said controlling step includes controlling said one or more actuators to deflect a portion of the paper away from said second conveyor in an ejected paper stream.*

*11. The method of claim 1, being further characterized as a method of sorting waste paper objects, wherein:*

*in said spreading step said one unit thick layer is substantially one paper object thick;*

*in said detecting step said layer of paper is a layer of paper objects; and*

*in said controlling step said sheet of paper is a paper object.*

*12. The method of claim 1, wherein:*

*the waste paper is provided in a stream including white paper and materials other than white paper; and*

*the controlling step includes controlling one or more actuators that direct the materials other than white paper out of the stream.*

*13. The method of claim 12, wherein:*

*said spreading step includes carrying the stream on a conveyor having a width; and*

*in the controlling step, said one or more actuators include an array of air jets spaced across the width of the conveyor, and said controlling step includes actuating an appropriate number of said air jets at an appropriate time to direct the materials other than white paper out of the stream.*

*14. The method of claim 1, wherein:*

*the waste paper is provided in a stream including white paper and materials other than white paper, wherein the stream is dominated by the materials other than white paper; and*

*the controlling step includes controlling one or more actuators that direct the white paper out of the stream.*

*15. The method of claim 14, wherein:*

*said spreading step includes carrying the stream on a conveyor having a width; and*

*in the controlling step, said one or more actuators include an array of air jets spaced across the width of the conveyor, and said controlling step includes actuating an appropriate number of said air jets at an appropriate time to direct the white paper out of the stream.*

*16. A method of sorting waste paper, comprising:*

*spreading waste paper out into a layer that is substantially one unit thick;*

*detecting the presence or absence of a predetermined optical characteristic as the layer of paper is passed by a sensor; and*

*controlling one or more actuators that direct a paper object based on the presence or absence of the predetermined optical characteristic.*

*17. A method of sorting waste paper objects, comprising:*

*spreading waste paper objects out into a layer that is substantially one waste paper object thick;*

*detecting the presence or absence of a predetermined optical characteristic as the layer of waste paper objects is passed by a sensor; and*

*controlling one or more actuators that direct the waste paper object based on the presence or absence of the predetermined optical characteristic.*

*18. The method of claim 17, further comprising:*

*providing the waste paper objects in a stream including white paper and materials other than white paper; and*

*wherein the controlling step includes controlling one or more actuators that direct the materials other than white paper out of the stream.*

*19. The method of claim 18, wherein:*

*said spreading step includes carrying the stream on a conveyor having a width; and*

*in the controlling step, said one or more actuators include an array of air jets spaced across the width of the conveyor, and said controlling step includes actuating an appropriate number of said air jets at an appropriate time to direct the materials other than white paper out of the stream.*

*20. The method of claim 17, further comprising:*

*providing the waste paper objects in a stream including white paper and materials other than white paper, wherein the stream is dominated by the materials other than white paper; and*

*wherein the controlling step includes controlling one or more actuators that direct the white paper out of the stream.*

*21. The method of claim 20, wherein:*

*said spreading step includes carrying the stream on a conveyor having a width; and*

*in the controlling step, said one or more actuators include an array of air jets spaced across the width of the conveyor, and said controlling step includes actuating an appropriate number of said air jets at an appropriate time to direct the white paper out of the stream.*

*22. A method of sorting waste paper objects, comprising:*

*providing a stream of waste paper objects in a layer that is substantially one waste paper object thick;*

*detecting the presence or absence of a predetermined optical characteristic as the layer of waste paper objects is passed by a sensor; and*

*controlling one or more actuators that direct the waste paper object based on the presence or absence of the predetermined optical characteristic.*

*23. The method of claim 22, wherein:*

*in said controlling step, each of said actuators includes an air jet.*

*24. The method of claim 23, wherein:*

*said providing step includes providing said layer on a conveyor having a width; and*

*in said controlling step, said air jets comprise an array of air jets spaced across the width of the conveyor.*

*25. The method of claim 23, wherein:*

*said detecting step includes communicating sensor signals from the sensor to a microprocessor; and*

*said controlling step comprises communicating control signals from the microprocessor to an array of solenoid valves associated with the air jets and thereby controlling a flow of air to the air jets.*

*26. The method of claim 22, further comprising:*

*conveying the layer of waste paper objects on a first conveyor and launching the layer of waste paper objects off the first conveyor across a gap to a second conveyor; and*

*wherein said controlling step includes controlling said one or more actuators to deflect a portion of the paper objects away from said second conveyor in an ejected paper object stream.*

*27. The method of claim 22, wherein:*

*in the providing step the stream includes white paper and materials other than white paper; and*

*the controlling step includes controlling one or more actuators that direct the materials other than white paper out of the stream.*

*28. The method of claim 27, wherein:*

*said providing step includes carrying the stream on a conveyor having a width; and*

*in the controlling step, said one or more actuators include an array of air jets spaced across the width of the conveyor, and said controlling step includes actuating an appropriate number of said air jets at an appropriate time to direct the materials other than white paper out of the stream.*

*29. The method of claim 22, wherein:*

*in the providing step the stream includes white paper and materials other than white paper, and the stream is dominated by the materials other than white paper; and*

*the controlling step includes controlling one or more actuators that direct the white paper out of the stream.*

*30. The method of claim 29, wherein:*

*said providing step includes carrying the stream on a conveyor having a width; and*

*in the controlling step, said one or more actuators include an array of air jets spaced across the width of the conveyor, and said controlling step includes actuating an appropriate number of said air jets at an appropriate time to direct the white paper out of the stream.*

* * * * *

UNITED STATES PATENT AND TRADEMARK OFFICE

CERTIFICATE OF CORRECTION

PATENT NO. : RE42,090 E
APPLICATION NO. : 11/139005
DATED : February 1, 2011
INVENTOR(S) : Bruner et al.

It is certified that error appears in the above-identified patent and that said Letters Patent is hereby corrected as shown below:

In column 1, line 13, in the specification, replace “Slates” with --States--.
In column 7, line 43, in the specification, replace “lake” with --take--.
In column 10, line 6, in claim 1, 5th line thereof, before “paper” insert --waste--.
In column 10, line 8, in claim 1, 7th line thereof, after “a sheet of” insert --the waste paper from the layer of waste--.
In column 11, line 41, in claim 16, 5th line thereof, after “the layer of” insert --waste--.
In column 11, line 44, in claim 16, 8th line thereof, after “object” insert --from the layer of waste paper--.
In column 11, line 53, in claim 17, 8th line thereof, replace “object” with --objects--.
In column 12, line 30, in claim 22, 8th line thereof, replace “object” with --objects--.

Signed and Sealed this
Fifteenth Day of March, 2011

David J. Kappos

David J. Kappos
*Director of the United States Patent and Trademark Office*